(12) United States Patent
Jang et al.

(10) Patent No.: US 8,711,348 B2
(45) Date of Patent: Apr. 29, 2014

(54) METHOD OF INSPECTING WAFER

(75) Inventors: Hwan-seok Jang, Suwon-si (KR); Jang-man Ko, Suwon-si (KR); Jun-seog Seong, Suwon-si (KR); Ho-bong Shin, Yongin-si (KR); Kil-su Lee, Seongnam-si (KR); Chang-hun Lee, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 509 days.

(21) Appl. No.: 13/115,355

(22) Filed: May 25, 2011

(65) Prior Publication Data

US 2011/0299069 A1 Dec. 8, 2011

(30) Foreign Application Priority Data

Jun. 4, 2010 (KR) ........................ 10-2010-0053035

(51) Int. Cl.
*G01N 21/00* (2006.01)
*G01N 21/956* (2006.01)
(52) U.S. Cl.
CPC ................................ *G01N 21/95607* (2013.01)
USPC ........................................................ 356/237.5
(58) Field of Classification Search
None
See application file for complete search history.

(56) References Cited

U.S. PATENT DOCUMENTS

| 5,105,147 | A | * | 4/1992 | Karasikov et al. | 356/401 |
| 5,308,222 | A | * | 5/1994 | Bacchi et al. | 414/783 |
| 5,699,447 | A | * | 12/1997 | Alumot et al. | 382/145 |
| 5,760,892 | A | * | 6/1998 | Koyama | 356/237.1 |
| 5,870,488 | A | * | 2/1999 | Rush et al. | 382/151 |
| 6,198,976 | B1 | * | 3/2001 | Sundar et al. | 700/59 |
| 6,760,976 | B1 | * | 7/2004 | Martinson et al. | 414/936 |
| 7,179,661 | B1 | * | 2/2007 | Satya et al. | 438/11 |
| 7,969,567 | B2 | * | 6/2011 | Yoshida et al. | 356/237.2 |
| 2004/0005212 | A1 | * | 1/2004 | Wu | 414/757 |
| 2008/0002875 | A1 | * | 1/2008 | Do | 382/144 |

FOREIGN PATENT DOCUMENTS

| JP | 08-293533 | 11/1996 |
| KR | 10-2002-0006746 A | 1/2002 |
| KR | 10-2007-0063935 A | 6/2004 |
| KR | 10-2005-0015144 A | 2/2005 |

* cited by examiner

*Primary Examiner* — Michael A Lyons
*Assistant Examiner* — Juan D Valentin, II
(74) *Attorney, Agent, or Firm* — Stanzione & Kim, LLP

(57) ABSTRACT

Wafer inspection method to perform wafer inspection based on photo map information. The wafer inspection method may include: detecting a sample center location on a wafer; compensating the detected sample center location to a compensated center location based on photo map information; and detecting defective dies included in the wafer based on the compensated center location.

11 Claims, 6 Drawing Sheets

FIG. 4A

| SAMPLE CENTER LOCATION | DEVICE 1 | DEVICE 2 | DEVICE 3 |
|---|---|---|---|
| X AXIS | 3021 | 2726 | 2819 |
| Y AXIS | 542 | 243 | 5638 |

FIG. 4B

| | INSPECTION DEVICE | DIE PITCH | SAMPLE CENTER LOCATION |
|---|---|---|---|
| BEFORE COMPENSATION | DEVICE 1 | X : 6099.821<br>Y : 6279.912 | X : 2751.212<br>Y : 330.8512 |
| | DEVICE 2 | X : 6099.211<br>Y : 6279.901 | X : 2851.142<br>Y : 330.2145 |
| AFTER COMPENSATION | DEVICE 1<br>DEVICE 2 | X : 6100.000<br>Y : 6280.000 | X : 3050.000<br>Y : 580.0000 |

METHOD OF INSPECTING WAFER

CROSS-REFERENCE TO RELATED APPLICATIONS

This application claims the benefit of Korean Patent Application No. 10-2010-0053035, filed on Jun. 4, 2010, in the Korean Intellectual Property Office, the disclosure of which is incorporated herein in its entirety by reference.

BACKGROUND OF THE INVENTION

1. Field of the Invention

The inventive concept relates to wafer inspection, and more particularly, to a method and system to inspect a defect of a wafer.

2. Description of the Related Art

A wafer inspection method is used to inspect defects on a wafer in each of operations of a wafer level process. Wafer inspection methods include a laser diffusion method, an optical image comparison method, and a method using an electron beam.

With increases of wafer sizes, the number of dies formed on a wafer may be increased. A defect image generated by inspecting a wafer is matched with an original image so as to determine whether a die is a defective die or not. Accordingly, as the number of dies is increased, time for analyzing defects may be increased.

SUMMARY OF THE INVENTION

The inventive concept provides a method and system of a wafer inspection, capable of improving defect analysis efficiency by inspecting a wafer based on photo map information.

Additional aspects and advantages of the present general inventive concept will be set forth in part in the description which follows and, in part, will be obvious from the description, or may be learned by practice of the general inventive concept.

Embodiments of the present general inventive concept provide a wafer inspection method comprising: detecting a sample center location on a wafer; compensating the detected sample center location to a compensated center location based on photo map information; and detecting defect dies included in the wafer based on the compensated center location.

The compensating of the detected sample center location may comprise compensating the detected sample center location to correspond to a predetermined center location based on the photo map information.

The photo map information may comprise wafer die pitch information and offset information.

The detecting of defective dies may comprise sequentially inspecting a plurality of dies on the wafer based on the photo map information. The inspecting of the plurality of dies may comprise inspecting the plurality of dies while sequentially increasing inspection coordinates by the die pitch from the sample center location.

The inspecting of the plurality of dies may comprise a single die test operation in which the plurality of dies on the wafer are sequentially tested while having a single die as an inspection unit. The inspecting of the plurality of dies may comprise a multi-die test operation in which the plurality of dies on the wafer are sequentially tested while having a plurality of dies as an inspection unit.

The detecting of defective dies of the wafer may comprise: determining whether a die is defective or not by irradiating a laser, an optical signal, or an electron beam to the wafer; and generating defect data based on a result of the determining.

The wafer inspection method may further comprise performing defect source analysis (DSA) on the defect data.

The wafer inspection method may further comprise electrical die sorting (EDS) by applying an electrical signal to the wafer.

Embodiments of the present general inventive concept also provide a wafer inspection system comprising a wafer inspection device that comprises: an inspection unit that detects a sample center location on a wafer, and inspects the wafer with respect to a compensated center location according to an inspection control signal, and generates defect data; and an inspection control unit that generates the inspection control signal, wherein the inspection control signal compensates the sample center location to the compensated center location according to photo map information.

The inspection unit may comprise: a defect test unit that detects the sample center location and tests the compensated center location according to the inspection control signal; and a defect analyzing unit that generates the defect data by receiving a defect image from the defect inspection unit and comparing the defect image with a photo map.

The defect test unit may generate a unit defect image with respect to a plurality of dies based on the compensated center location and information about a die pitch included in the photo map information.

The defect test unit may sequentially perform inspection from the compensated center location based on the inspection control signal while having a single die as an inspection unit.

The defect test unit may sequentially perform inspection from the compensated center location based on the inspection control signal while having a plurality of dies as an inspection unit.

The defect test unit may comprise an inspection device for irradiating a laser, an optical signal, or an electron beam with respect to the compensated center location.

The wafer inspection system may further comprise a host managing unit performing defect source analysis (DSA) on the defect data.

The inspection unit may generate a plurality of pieces of defect data generated when forming a plurality of patterns on a wafer, and the host managing unit may perform DSA on the plurality of pieces of defect data based on the compensated center location.

The wafer inspection system may further comprise an electrical die sorting unit that performs electrical die sorting by applying an electrical signal to the wafer.

The wafer inspection system may further comprise a photo device that forms a pattern on the wafer based on the photo map information.

BRIEF DESCRIPTION OF THE DRAWINGS

Exemplary embodiments of the present inventive concept will be more clearly understood from the following detailed description taken in conjunction with the accompanying drawings in which:

FIGS. 4A and 4B illustrate compensation of a sample center location according to some example embodiments of the inventive concept;

DETAILED DESCRIPTION OF THE PREFERRED EMBODIMENTS

Figure 1:
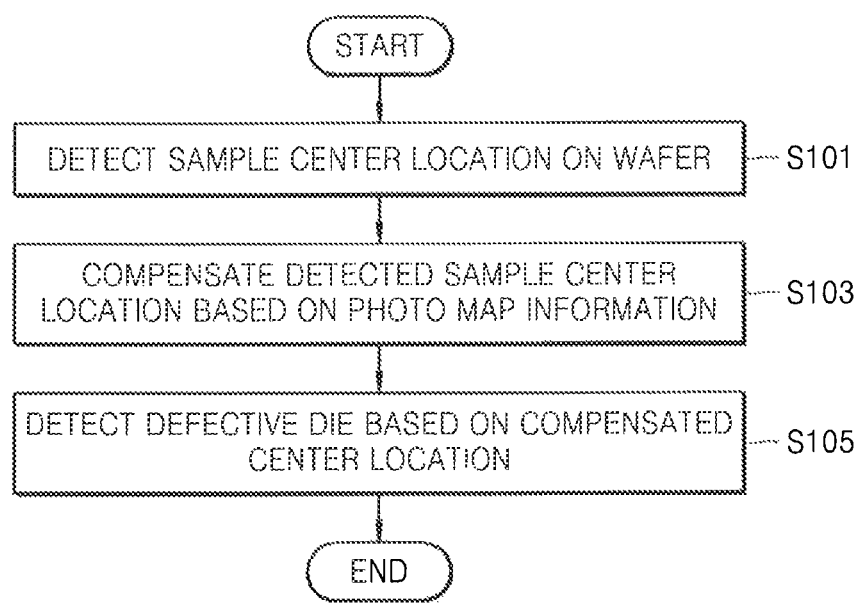
FIG. 1 is a flowchart illustrating a wafer inspection method according to some example embodiments of the inventive concept.

Reference will now be made in detail to the embodiments of the present general inventive concept, examples of which are illustrated in the accompanying drawings, wherein like reference numerals refer to the like elements throughout. The embodiments are described below in order to explain the present general inventive concept while referring to the figures.

The embodiments are provided so that this disclosure will be thorough and complete, and will fully convey the concept of the inventive concept to those skilled in the art. The inventive concept may be embodied in many different forms and should not be construed as being limited to the embodiments set forth herein; rather, these embodiments are provided so that this disclosure will be thorough and complete, and will fully convey the concept of the inventive concept to those skilled in the art.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, members, elements, and/or groups, but do not preclude the presence or addition of one or more other features, integers, steps, members, elements, and/or groups thereof.

In the present description, terms such as 'first', 'second', etc, are used to describe various members, regions, layers, portions, and/or elements. However, it is obvious that the members, regions, layers, portions, and/or elements should not be defined by these terms. The terms are used only for distinguishing one member, component, region, layer, or portion from another member, component, region, layer, or portion. Thus, a first member, component, region, layer, or portion which will be described may also refer to a second member, region, layer, portion or element, without departing from the teaching of the inventive concept. For example, without departing from the teaching of the inventive concept, a first element may be referred to as a second element, or a second may be referred to as a first element.

It will be understood that when a component such as a layer, a region, or a substrate is referred to as being "on", "connected to", or "coupled to" another component throughout the specification, it can be directly "on", "connected to", or "coupled to" the other component, or intervening layers may also be present. On the other hand, when a component is referred to as being "directly on", "directly connected to", or "directly coupled to" another component, it will be understood that no intervening layer is present. Other expressions about relationships between elements, "between ~" and "directly between ~" or "adjacent to ~" and "directly adjacent to ~" should be understood likewise.

The terms used in the present specification are merely used to describe particular embodiments, and are not intended to limit the inventive concept. An expression used in the singular encompasses the expression of the plural, unless it has a clearly different meaning in the context. In the present specification, it is to be understood that the terms such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

When an embodiment may be implemented in another, different way, a function or operation described to be within a particular block may be performed in a different order than described in the flowchart. For example, two continuous blocks may be performed at the same time substantially, or the blocks may be performed in a reverse order according to a relevant function or operation.

Embodiments of the inventive concept are described herein with reference to cross-section illustrations that are schematic illustrations of idealized embodiments of the inventive concept. As such, variations from the shapes of the illustrations as a result, for example, of manufacturing techniques and/or tolerances, are to be expected. Thus, embodiments of the inventive concept should not be construed as limited to the particular shapes of regions illustrated herein but are to include deviations in shapes that result, for example, from manufacturing.

FIG. 1 is a flowchart illustrating a wafer inspection method according to an embodiment of the general inventive concept.

Referring to FIG. 1, a sample center location on a wafer is detected (operation S101). The sample center location is a starting point that is detected to conduct wafer inspection, and an arbitrary point may be detected as the sample center location. The sample center location may vary according to wafer inspecting devices. For example, different wafer inspecting devices may each designate any of dies formed at various positions on a wafer as an origin die. Alternatively, even when different wafer inspecting devices each designate the same die as an origin die on a wafer, various coordinates may be detected as sample center locations due to mechanical errors in the wafer inspecting devices. The sample center location may be represented based on X-axis and Y-axis coordinates.

When wafer inspection is performed with respect to the detected sample center location, the wafer inspection may be performed on coordinates different from where a pattern or dies are formed during a photo process. Accordingly, a matching operation is to be performed using defect maps and photo maps generated based on inspection results. In the matching operation, an error may be caused due to different reference coordinates, and time for manufacturing a whole wafer may increase due to time required for the matching operation.

With reference to a pattern formed on a wafer, a defect map may be generated. Accordingly, when a plurality of patterns are formed on a wafer in a wafer manufacturing process, and thus a plurality of defect maps are generated, time for matching each defect map with each photo map and analyzing the same is increased, thereby decreasing a wafer manufacturing yield.

The detected sample center location is compensated based on photo map information (operation S103). For example, the photo map information may include die pitch information and offset information. The photo map information may vary according to a wafer photo process used, and will be described later with reference to FIG. 2.

The sample center location may be compensated to a left lower coordinate of an origin die of a wafer formed in a photo process, based on the photo map information, to be set as a compensated center location. However, a method of compensating a sample center location is not limited thereto.

Furthermore, a coordinate that is a predetermined multiple of a die pitch from the compensated center location may be designated as a next inspection coordinate. The predetermined multiple of the die pitch may vary according to the wafer inspection devices, and may correspond to a size of a unit defect image. Inspection coordinates may be set based on the photo map information. However, since a wafer inspection method is performed with respect to a single die or a plurality of dies according to the type of the wafer inspection method, inspection coordinates may be set variously according to the wafer inspection methods used, for example, coordinates may be set according to the number of dies included in one wafer inspection, that is the number of dies which are simultaneously inspected.

Wafer inspection is performed based on the compensated center location (operation S105). The wafer inspection refers to inspecting whether a defect is generated in the pattern formed on a wafer, and examples of wafer inspection methods include a brightness inspection method using optics, a process using a laser, and a process using an electron beam. In a wafer inspection method using an electron beam, an electron beam is irradiated to a wafer, and based on electrons emitted from the wafer, defects of the wafer may be detected. For example, an electron beam may be irradiated to a wafer by using a scanning electronic microscope (SEM) and electrons reflected from the wafer may then be observed.

At least one unit defect image is included in a defect image, and the defect image forms a defect map that is compared with a photo map. Defect data may be generated by comparing the defect map to the photo map.

According to the wafer inspection method and a wafer inspection system according to some example embodiments of the inventive concept, the sample center locations are compensated and a defect image is formed based on an identical compensated center location. Defect images generated based on the identical compensated center locations have the same coordinates as a photo map, and thus the defect images need not be matched with the photo map additionally. Accordingly, time for defect source analysis (DSA) on a plurality of pieces of defect data may be reduced, thereby increasing a wafer manufacturing yield.

Figure 2:
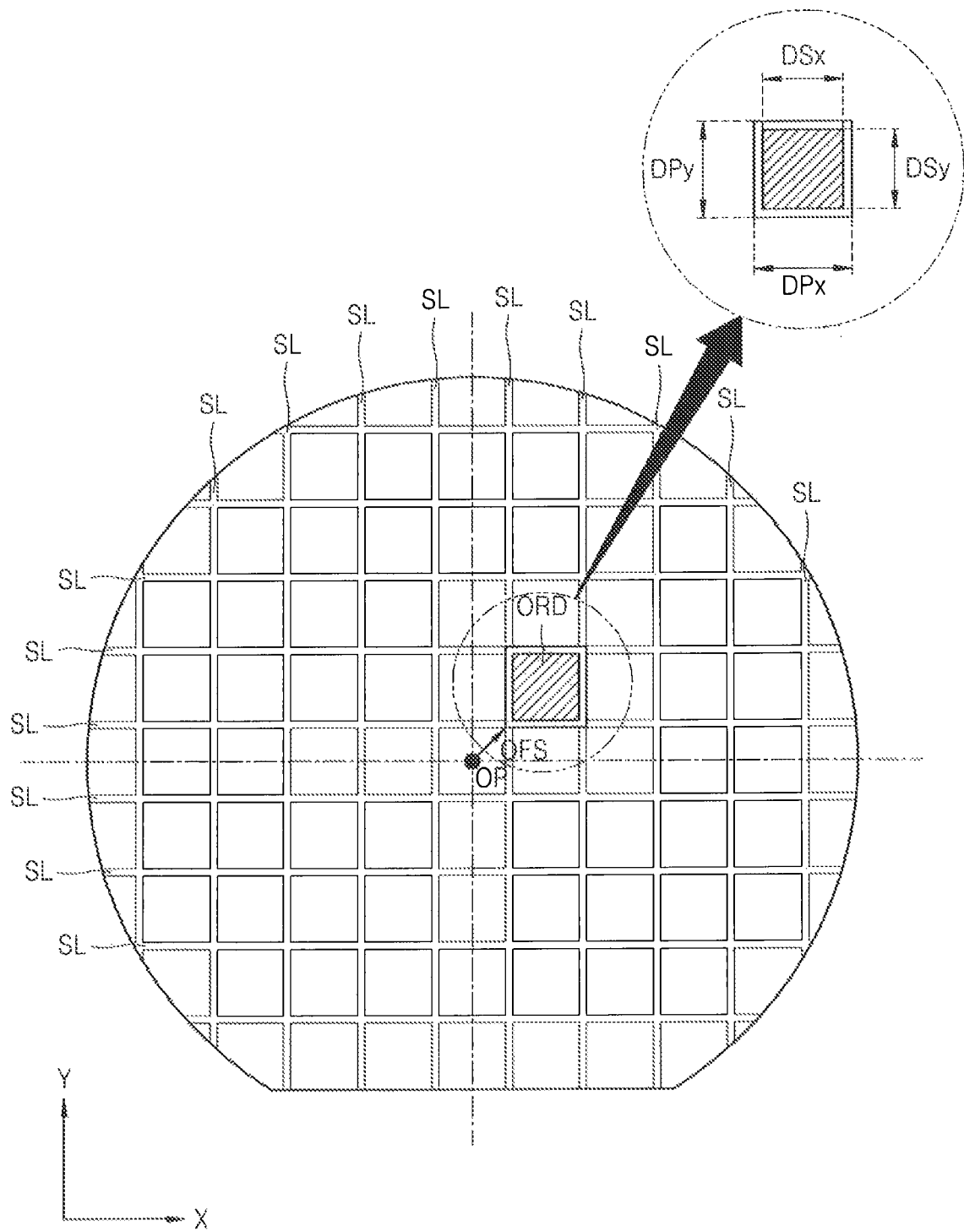
FIG. 2 is a schematic view illustrating photo map information according to some example embodiments of the inventive concept.

FIG. 2 is a diagram describing a photo map according to some example embodiments of the inventive concept.

Referring to FIG. 2, a plurality of dies formed on a wafer may be used to form chips corresponding to the respective die size (DS), and each of the dies are bordered by scribe lines (SL).

When forming a pattern on a wafer, a die pitch DP may be defined by the sum of the die size DS and a width of the scribe lines SL. The die pitch may form a single chip.

In a photo process, a shot may be defined based on the die pitch DP. For example, one shot may include at least one die pitch DP. An origin die ORD may be spaced apart from an origin point OP by a distance corresponding to an offset OFS. The die size DS, the die pitch DP, and the offset OFS may be denoted by X and Y coordinates, and be included in photo map information.

The offset OFS may have any of various values according to a photo device used, and the die pitch DP and the die size DS each having any of various values may be detected according to an inspection device used. The photo device may perform a photo process according to photo map information that is previously stored, or perform a photo process by receiving photo map information from an external device.

The number of dies that are inspected at a time may vary according to an inspection device used. Thus, a defect image may be generated based on a unit defect image having any of various sizes corresponding to the multiple of the predetermined die pitch DP. The number of dies being inspected at a time by the inspection device may vary according to sizes of chips on the wafer. For example, when four dies are inspected by the inspection device at the same time, a unit defect image may be generated with respect to the four dies. The defect image may include a plurality of unit defect images. For example, wafer inspection coordinates may be generated based on the unit defect images.

According to some example embodiments of the inventive concept, the inspection coordinates may be generated independent of the size of a unit defect image, and thus a plurality of overlapping defect images with respect to a plurality of dies may be generated.

Various patterns may be formed on a wafer based on photo map information. According to the wafer inspection method and the wafer inspection system, a compensated center location may be set with respect to a wafer in which a pattern is formed based on the photo map information, and then the wafer inspection is performed. When performing wafer inspection based on the compensated center location, a plurality of defect maps are generated based on a single compensated center location, and thus time for matching each of the defect maps with a photo map and analyzing defects to generate defect data may be minimized.

Figure 3:
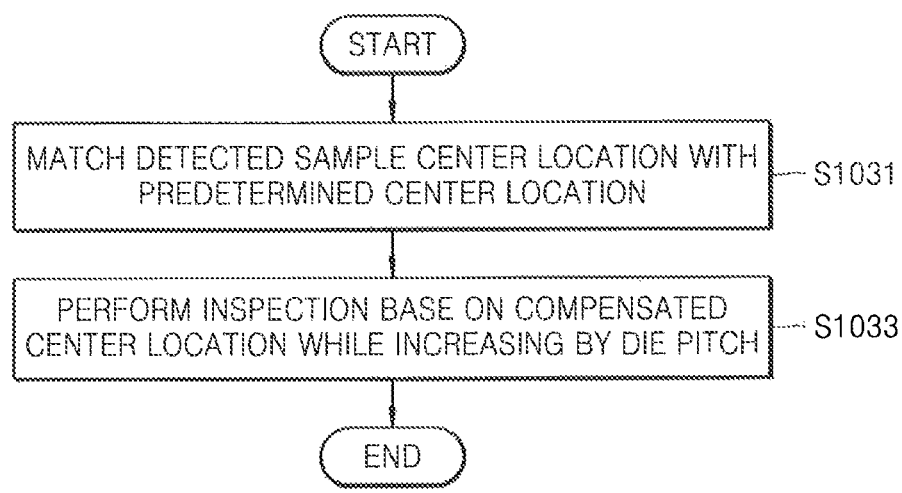
FIG. 3 is a flowchart illustrating an operation of compensating a sample center location according to some example embodiments of the inventive concept.

FIG. 3 is a flowchart illustrating an operation of compensating sample center location according to some example embodiments of the inventive concept.

Referring to FIG. 3, a sample center location that is detected based on photo map information is matched to a predetermined set center location to set a compensated center location (operation S1031). The predetermined center location may vary according to the photo map information. Also, a die pitch may also be variously defined according to the photo map information. For example, the detected die pitch may have a value different from a value of a die pitch used in an actual photo process, which is predetermined according to the photo map information. When the detected die pitch and the predetermined die pitch are different from each other, an error may occur when inspecting a plurality of dies, and thus the die pitch needs to be compensated.

Wafer inspection is performed with respect to the compensated center location (operation S1033). During the wafer inspection based on the compensated center location, wafer inspection with respect to a plurality of dies may be performed. As described above, the die pitch included in the photo map information used in the photo process and the die pitch detected by the wafer inspection device may have different values. The number of dies being inspected by the wafer inspection device at a time may vary according to some example embodiments of the inventive concept, and thus the wafer inspection coordinates may be sequentially compensated so as to correspond to sizes of unit defect images based on the die pitch included in the photo map information.

For example, when coordinates of a compensated center location is (ORDx, ORDy), and a die pitch is (DPx, DPy), the wafer inspection may be performed in units of a single die.

The wafer inspection may be sequentially performed while increasing the compensated center location by a predetermined die pitch. Wafer inspection may be performed in the order of (ORDx, ORDy), (ORDx+DPx, ORDy), (ORDx+2*DPx, ORDy) . . . , (ORDx, ORDy+DPy), (ORDx+DPx, ORDy+DPy), (ORDx+2*DPx, ORDy+DPy) . . . , (ORDx, ORDy+2*DPy), (ORDx+DPx, ORDy+2*DPy), and (ORDx+2*DPx, ORDy+2*DPy). However, during this inspection, one die is used as an inspection die, and an example of a single die test operation having a unit defect image of (DPx, DPy) is described; in a multi-die test operation in which a plurality of dies are inspected as one inspection unit, coordinates that sequentially increase may vary.

For example, wafer inspection may be performed while having nine dies as an inspection unit. In this case, a single defect image of (3*DPx, 3*DPy) may be generated, and wafer inspection may be performed sequentially while increasing inspection coordinates by a die pitch of a predetermined multiple like (ORDx, ORDy), (ORDx+3*DPx, ORDy), (ORDx+6*DPx, ORDy), (ORDx+9*DPx, ORDy) . . . , (ORDx, ORDy+3*DPy), (ORDx+3*DPx, ORDy+3*DPy), (ORDx+6*DPx, ORDy+3*DPy), (ORDx+9*DPx, ORDy+3*DPy) . . . , (ORDx, ORDy+6*DPy), (ORDx+3*DPx, ORDy+6*DPy), (ORDx+6*DPx, ORDy+6*DPy), ORDx+9*DPx, ORDy+6*DPy). If the die pitch is not compensated, errors included in the inspection coordinates may increase as inspection is performed sequentially with respect to the inspection coordinates.

FIGS. 4A and 4B illustrate compensation of a sample center location according to some example embodiments of the inventive concept.

Referring to FIG. 4A, when using different inspection devices, different sample center locations are detected with respect to a single wafer.

A first device DEVICE 1 and a second device DEVICE 2 designate the same die as an origin die but due to mechanical errors, a sample center location at (3021, 542) is detected by the first device DEVICE 1, and a sample center location at (2726, 243) is detected by the second device DEVICE 2. The first device DEVICE 1 and the second device DEVICE 2 may preferably detect the same sample center location, but even with the same origin die, different inspection devices may detect different sample center locations.

Also, when different origin dies are set, a sample location at (2819, 5638) may be detected by a third device DEVICE 3, which is relatively far away from the above-described sample center locations.

When defect data is generated without compensating each of the detected sample center locations, a defect map having different coordinates from a photo map may be generated, and thus time may be required to match the different coordinates.

FIG. 4B is a schematic view illustrating sample center locations before and after compensation.

Referring to FIG. 4B, the sample center locations of the first device DEVICE 1 and the second device DEVICE 2 before compensation have relatively small error. For example, a sample center location at (2751.212, 330.8512) is detected by the first device DEVICE 1, and a sample center location at (2851.142, 330.2145) is detected by the second device DEVICE 2, which is a relatively small error. Also, a die pitch of (6099.821, 6279.912) is detected by the first device DEVICE 1, and a die pitch of (6099.211, 6279.901) is detected by the second device DEVICE 2. Errors of the die pitches of the devices may be negligible, but may also accumulate while generating a plurality of inspection coordinates based on the die pitches.

The sample center locations after compensation, that is, compensated center locations of the first device DEVICE 1 and the second device DEVICE 2, are the same, (3050, 580), and die pitches of the first device DEVICE 1 and the second device DEVICE 2 have become the same, (6100, 6280).

According to embodiments of the inventive concept, the sample center locations and the die pitches may be compensated to integers.

Figure 5:
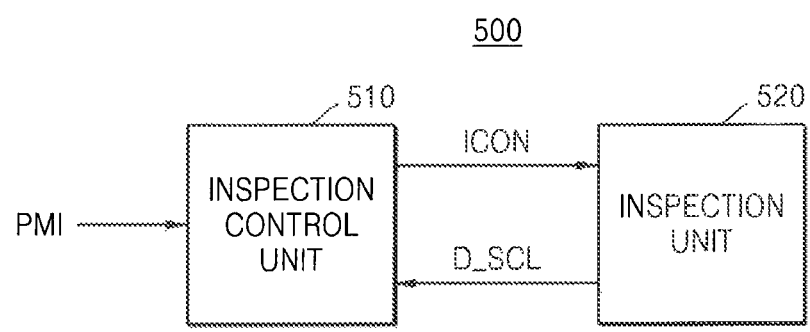
FIG. 5 is a block diagram illustrating a wafer inspection device according to some example embodiments of the inventive concept.

FIG. 5 is a block diagram illustrating a wafer inspection device 500 according to some example embodiments of the inventive concept.

Referring to FIG. 5, the wafer inspection device 500 may include an inspection control unit 510 and an inspection unit 520.

The inspection control unit 510 receives photo map information PMI that is input by an external device such as a host inspection device to generate an inspection control signal ICON. Also, the inspection control unit 510 may receive a sample center location D_SCL detected from the inspection unit 520. When the detected sample center location D_SCL corresponds to a predetermined center location, the inspection unit 520 is instructed to perform wafer inspection without compensation. However, even when the detected sample center location D_SCL is substantially the same as the predetermined center location, a die pitch may be compensated, and thus a compensation operation may be performed.

The inspection control signal ICON is applied to the inspection unit 520 to perform inspection with respect to a compensated center location C_SCL. Inspection of the compensated center location C_SCL may be performed using any of various inspection methods according to a configuration of the inspection unit 520, and coordinates configuration of the inspection unit 520 may vary according to whether a single die test or a multi-die test is performed.

Figure 6:
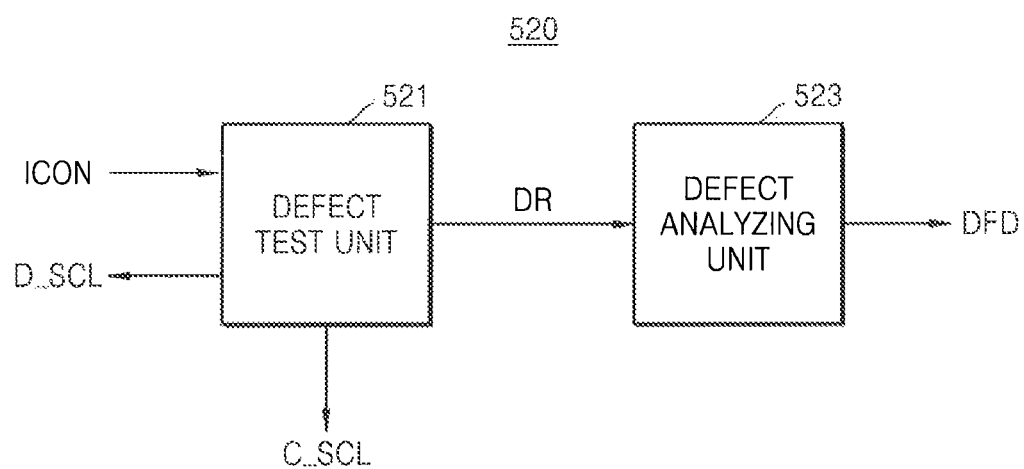
FIG. 6 is a block diagram illustrating an inspection unit illustrated in FIG. 5, according to an embodiment of the inventive concept.

FIG. 6 is a block diagram illustrating the inspection unit 520 illustrated in FIG. 5, according to some example embodiments of the inventive concept.

Referring to FIG. 6, the inspection unit 520 may include a defect test unit 521 and a defect analyzing unit 523.

The defect test unit 521 may generate a defect image DR used to determine whether a defect of a wafer is present based on an inspection control signal ICON. For example, the defect test unit 521 may irradiate a laser, an optical signal, or an electron beam to the wafer to generate the defect image DR. Accordingly, the defect test unit 521 may include an inspection device that irradiates a laser, an optical signal, or an electron beam to a wafer. The defect image DR may include at least one unit defect image as described above, and the unit defect image may have a size corresponding to a predetermined die pitch on X and Y axes. Also, the defect test unit 521 may detect the sample center location D_SCL and provide the detected sample center location D_SCL to the inspection control unit 510 of FIG. 5.

For example, the defect test unit 521 may generate a unit defect image from the compensated center location C_SCL while sequentially increasing inspection coordinates by predetermined die pitches according to an inspection unit of a defect inspection.

The defect analyzing unit 523 may determine whether each of dies formed on a wafer has a defect, by obtaining the defect image DR and performing a die-to-die test. The defect analyzing unit 523 may generate defect data DFD regarding whether there is a defect corresponding to each of the dies.

The defect data DFD may be generated when a pattern is formed on each wafer. During a line process, the dies may be analyzed to determine whether they are defective or not with respect to each operation.

According to some example embodiments of the present inventive concept, analysis of the defect data DFD in the defect analyzing unit 523 may be performed in an external device.

Figure 7:
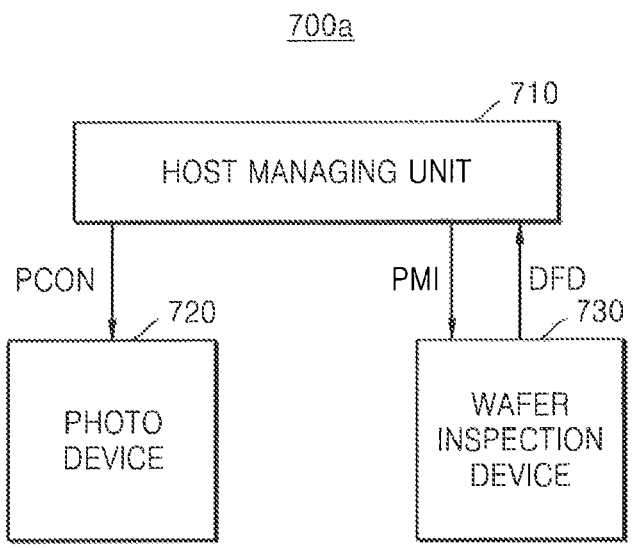
FIGS. 7 and 8 are block diagrams illustrating a wafer inspection system according to some example embodiments of the inventive concept.

FIG. 7 is a block diagram illustrating a wafer inspection system 700*a* according to another embodiment of the inventive concept.

Referring to FIG. 7, the wafer inspection system 700*a* may include a host managing unit 710, a photo device 720, and a wafer inspection device 730.

The wafer inspection system 700*a* may control a photo process and a wafer inspection process, and may determine whether a finally manufactured semiconductor chip has a defect.

The host managing unit 710 may control the photo process by providing a photo control signal PCON to the photo device 720. The photo control signal PCON, which the photo process is performed according to, may include photo map information PMI.

The photo device 720 performs the photo process based on the photo map information PMI.

The wafer inspection device 730 performs wafer inspection by receiving the photo map information PMI from the host managing unit 710. The wafer inspection device 730 may have the above-described configuration, and may compensate a sample center location to a compensated center location based on the photo map information PMI and generate defect data DFD by performing a wafer inspection with respect to the compensated center location.

The host managing unit 710 may perform defective source analysis (DSA) for comprehensive analysis of defects with respect to patterns on an entire wafer on the received defect data DFD. According to some example embodiments of the inventive concept, the host managing unit 710 may receive a defect image DR from the wafer inspection device 730 to determine whether dies are defective, thereby generating defect data DFD.

Since the host managing unit 710 controls the photo device 720 and the wafer inspection device 730 to use the photo map information PMI used in the photo process, when inspecting wafers, the dies in each of wafer manufacturing processes do not have to be matched, and thus a defect of a wafer may be quickly tested.

Figure 8:
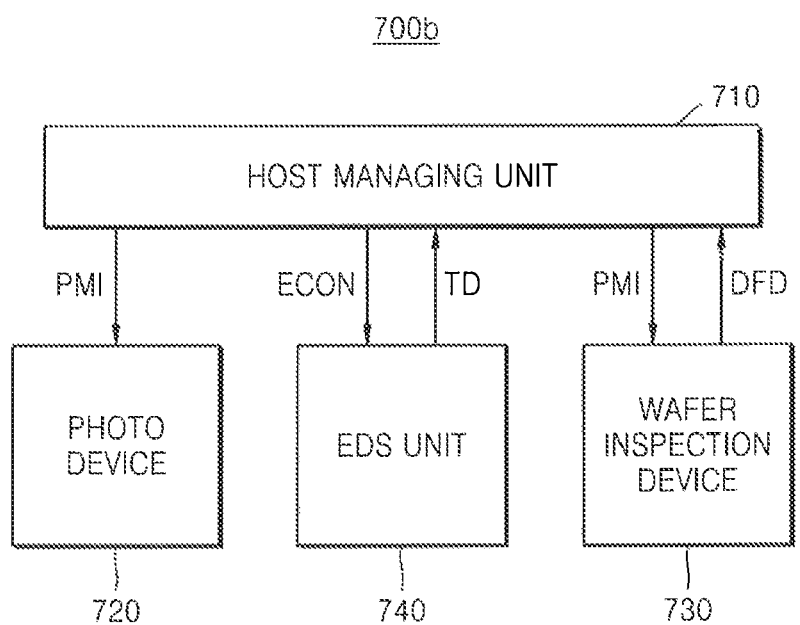

FIG. 8 is a block diagram illustrating a wafer inspection system 700*b* according to other example embodiments of the inventive concept.

Referring to FIG. 8, the wafer inspection system 700*b* may include a host managing unit 710, a photo device 720, a wafer inspection device 730, and an electrical die sorting (EDS) unit 740. In FIG. 8, like reference numerals as in FIG. 7 denote like elements, and thus a detailed description thereof will be omitted.

The wafer inspection system 700*b* provides photo map information PMI to the photo device 720 so as to perform a photo process, and provides the photo map information PMI to the wafer inspection device 730 to receive defect data DFD.

The wafer inspection device 730 may have substantially the same configuration as the wafer inspection device 500 illustrated in FIG. 5, and performs wafer inspection on a compensated center location that is compensated based on the photo map information PMI used in the photo process to thereby increase a matching rate of defect data.

Compared to the wafer inspection system 700*a* of FIG. 7, the wafer inspection system 700*b* illustrated in FIG. 8 may further include an electrical die sorting unit 740. The electrical die sorting unit 740 may receive an electric inspection control signal ECON from the host managing unit 710, and may test whether dies are defective based on the received signal. The electrical die sorting unit 740 may perform an electrical die sorting test after a wafer line process is completed, and determine whether a chip formed on a wafer operates normally after the defect data DFD is analyzed by the wafer inspection device 730. The electrical die sorting unit 740 may generate test data TD with respect to a test result and provide the same to the host managing unit 710.

Accordingly, according to the wafer inspection method of some example embodiments of the inventive concept as provided herein, wafer inspection is performed first with respect to a compensated center location based on photo map information, and then a die pitch is compensated to generate a defect image to thereby reduce time for matching when matching the defect image with a photo map to generate defect data. Also, when generating a plurality of pieces of defect data, time required for defect analysis may be reduced.

Also, the wafer inspection device according to the various embodiments of the inventive concept performs wafer inspection based on a single compensated center location to generate defect images with respect to the identical coordinates. When a plurality of wafer patterns are formed, time for generating a plurality of pieces of defect data may be reduced. Also, the wafer inspection system including the wafer inspection device of the various embodiments of the inventive concept may control a photo process and a wafer inspection operation based on photo map information to thereby obtain a defect image with an increased matching rate.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

What is claimed is:

1. A wafer inspection method comprising:
   detecting a sample center location on a wafer;
   compensating the detected sample center location to a compensated center location based on photo map information, the compensating of the detected sample center location including compensating the detected sample center location to correspond to a predetermined center location based on the photo map information, wherein the photomap information includes in die size DS and die pitch DP denoted in X and Y coordinates such that an offset from an original point on the wafer is determined; and
   detecting defective dies included on the wafer based on the compensated center location.

2. The wafer inspection method of claim 1, wherein the detecting of defective dies comprises sequentially inspecting a plurality of dies on the wafer based on the photo map information.

3. The wafer inspection method of claim 2, wherein the inspecting of the plurality of dies comprises inspecting the plurality of dies while sequentially increasing inspection coordinates by the die pitch from the sample center location.

4. The wafer inspection method of claim 3, wherein the inspecting of the plurality of dies comprises a single die test operation in which the plurality of dies on the wafer are sequentially tested while having a single die as an inspection unit.

5. The wafer inspection method of claim 3, wherein the inspecting of the plurality of dies comprises a multi-die test operation in which the plurality of dies on the wafer are sequentially tested while having a plurality of dies as an inspection unit.

6. The wafer inspection method of claim 1, wherein the detecting of defective dies of the wafer comprises:
   determining whether a die is defective or not by irradiating a laser, an optical signal, or an electron beam to the wafer; and
   generating defect data based on a result of the determining.

7. The wafer inspection method of claim 6, further comprising:
   performing defect source analysis (DSA) on the defect data.

8. The wafer inspection method of claim 1, further comprising:
   electrical die sorting (EDS) by applying an electrical signal to the wafer.

9. A wafer inspection method comprising:
   compensating a sample center location of a wafer based on photo map information, the compensating of the detected sample center location including compensating the detected sample center location to correspond to a predetermined center location based on the photo map information, wherein the photo map information includes a die size DS and a die pitch DP denoted in X and Y coordinates such that an offset from an original point on the wafer is determined; and
   detecting defective dies included on the wafer based on the compensated center location.

10. The wafer inspection method of claim 9, wherein the photo map information is previously stored information.

11. The wafer inspection method of claim 9, wherein the photo map information is provided from an external device.

* * * * *